United States Patent [19]

Prosky

[11] 4,403,296
[45] Sep. 6, 1983

[54] MEASURING AND DETERMINATION DEVICE FOR CALCULATING AN OUTPUT DETERMINATION BASED ON A MATHEMATICAL RELATIONSHIP BETWEEN MULTIPLE DIFFERENT INPUT RESPONSIVE TRANSDUCERS

[75] Inventor: Howard S. Prosky, Englewood, Colo.

[73] Assignee: Electromedics, Inc., Englewood, Colo.

[21] Appl. No.: 217,656

[22] Filed: Dec. 18, 1980

[51] Int. Cl.³ .................... G01K 7/16; G06F 15/353
[52] U.S. Cl. ................................ 364/573; 364/557; 374/181; 374/109
[58] Field of Search ............... 364/573, 557; 73/341, 73/342, 359 R, 359 A, 361, 362 AR

[56] References Cited

U.S. PATENT DOCUMENTS

| | | | |
|---|---|---|---|
| 2,987,704 | 6/1961 | Gimpel et al. | 340/172.5 |
| 3,699,318 | 10/1972 | Underkoffler et al. | 235/151.1 |
| 3,921,453 | 11/1975 | Platzer, Jr. | 73/361 |
| 4,022,063 | 5/1977 | West et al. | 73/362 |
| 4,060,715 | 11/1977 | Scott | 364/557 |
| 4,114,442 | 9/1978 | Group | 364/557 X |
| 4,122,719 | 10/1978 | Carlson et al. | 364/557 X |
| 4,130,019 | 12/1978 | Nitschke | 73/341 |
| 4,133,700 | 1/1979 | Hollander et al. | 73/361 |
| 4,158,965 | 6/1979 | Prosky | 73/362 |
| 4,161,880 | 7/1979 | Prosky | 73/342 |
| 4,179,745 | 12/1979 | Wertele | 364/557 X |
| 4,211,113 | 7/1980 | Harrison | 364/557 X |
| 4,282,578 | 8/1981 | Payne et al. | 364/573 |
| 4,286,465 | 9/1981 | Thomae | 364/557 X |
| 4,288,853 | 9/1981 | Useugi | 364/557 |
| 4,293,916 | 10/1981 | Del Re et al. | 364/557 X |
| 4,298,947 | 11/1981 | Tamura et al. | 364/557 |

Primary Examiner—Edward J. Wise
Attorney, Agent, or Firm—Crandell & Polumbus

[57] ABSTRACT

An electronic measuring device utilizes multiple different transducers for supplying signals exhibiting predetermined and typically nonlinear relationships to the multiple input variables sensed by the transducers. The measuring device includes a microcomputer containing stored linearizing information therein relating to the predetermined nonlinear relationship of the signals supplied by the transducers and the variables sensed by the transducers. The microcomputer linearizes each of the signals supplied by the transducers and thereby obtains highly accurate signals indicative of the variables sensed. Depending upon the ultimate determination to be obtained by the device, the linearized signals representative of the input variables may be employed in a polynomial equation calculation conducted by the computer to obtain the output determination. The polynomial equation includes a plurality of constants, and different values of the constants are stored in memory for various segments of the curve defined by the polynomial equation. The values of the constants also constitute stored linearizing information and the different values are available for use in the calculation to obtain the best accuracy of simulating the mathematical curve of the polynomial equation to the actual curve of the quantity under determination. The device is particularly useful as an electronic thermometer employing a thermocouple for measuring temperature and a thermistor for measuring the cold electrical connection junction of the thermocouple. The device is also advantageously used to measure density altitude, dew point and superheat temperature, among other things.

21 Claims, 3 Drawing Figures

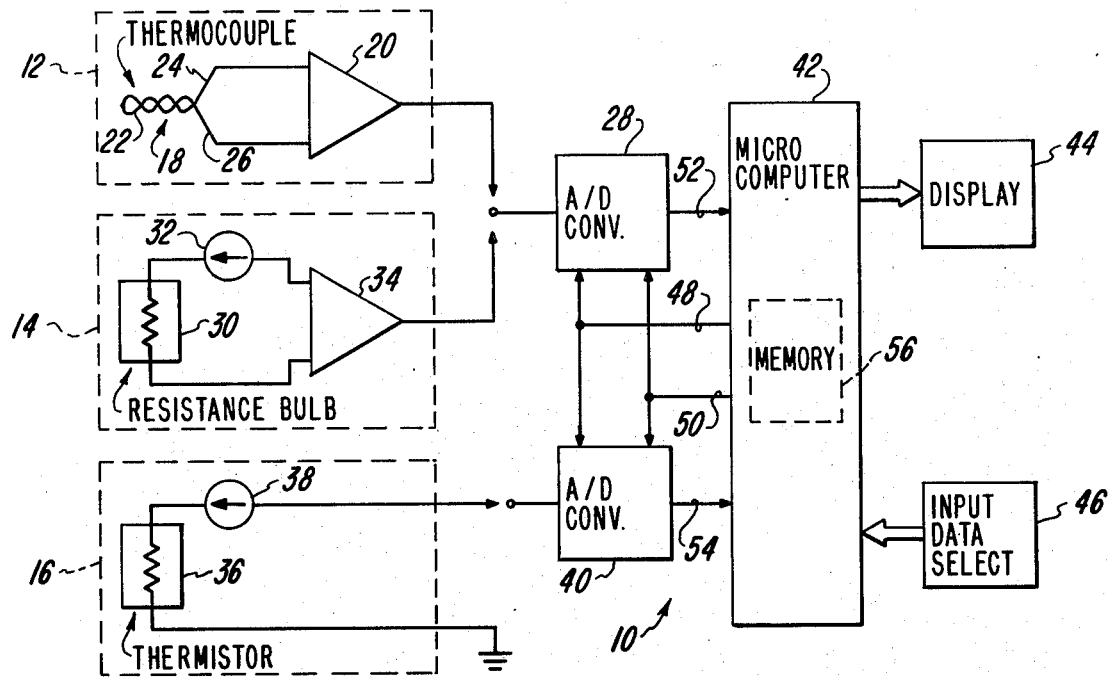
Fig_1
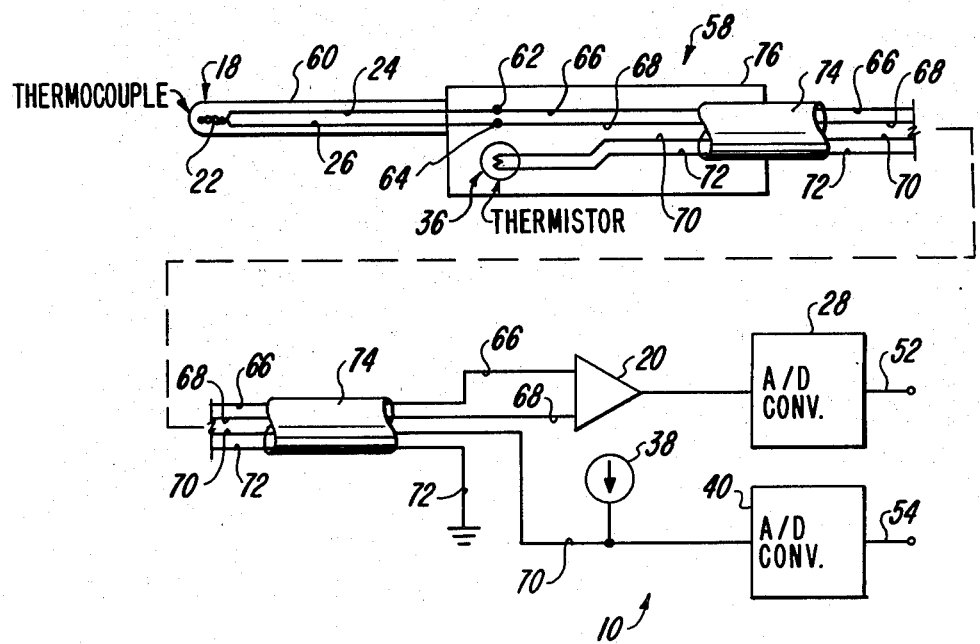
Fig_2

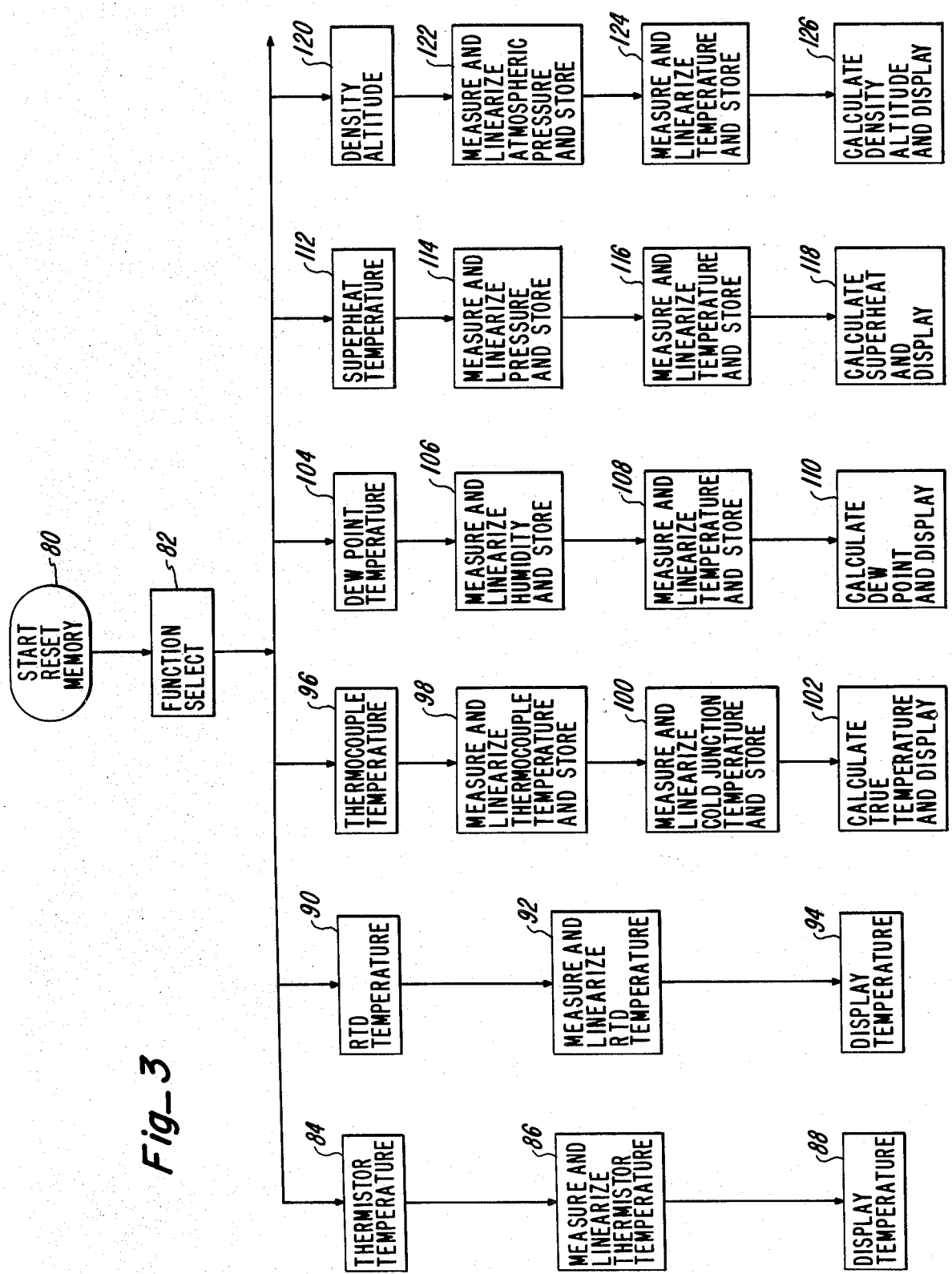

MEASURING AND DETERMINATION DEVICE FOR CALCULATING AN OUTPUT DETERMINATION BASED ON A MATHEMATICAL RELATIONSHIP BETWEEN MULTIPLE DIFFERENT INPUT RESPONSIVE TRANSDUCERS

This invention pertains to a measurement and determination device providing a highly accurate output determination or measurement based on a nonlinear or polynomial relationship between multiple different input variables, and which accurately accounts for potentially nonlinear relationships between the input variables and the signals supplied by transducers related to the input variables sensed. More specifically, the invention pertains to an electronic measurement and determination device which includes an internal microcomputer exercising control over the device for the operative purposes of, first, linearizing each of multiple different input signals supplied by transducers which nonlinearly relate the input signals to the input variables sensed, and secondly, calculating the output determination or measurement based on a nonlinear or polynomial relationship of the linearized input signals. The device of the present invention is particularly useful for measuring temperature, particularly with a thermocouple transducer where an additional temperature measurement for cold junction compensation must be obtained, for measuring dew point based on a polynomial relationship of temperature and humidity, for measuring superheat temperature based on a polynomial relationship of temperature and pressure, and for measuring density altitude based on a polynomial relationship of temperature and pressure.

In the field of electronic thermometers, the most commonly used types of input transducers are thermistors, thermocouples and resistance bulb elements. All of these transducers inherently relate the input temperature to the supplied output signal in a predetermined nonlinear relationship. This nonlinear relationship is typically defined by polynomial equation of at least a second order. The nonlinear relationship will cause electronic measurement errors unless the signal from the transducer is subjected to linearization. U.S. Pat. No. 4,161,880 for a Linearized Digital Thermometer, assigned to the assignee of the present invention, discloses one reliable, compact and relatively inexpensive device utilizing a microcomputer for linearizing and obtaining electronic measurement signals from a single nonlinear input transducer, such as a thermistor or a resistance bulb. Thermocouple transducers, however, present additional problems because the thermocouple typically requires two temperature measurements.

A thermcouple consists of two metallically dissimilar wires connected at a temperature measurement or hot junction. The metallic properties of the two dissimilar conductors at the temperature measurement junction generate a voltage which varies in a predetermined relationship, typically nonlinear or polynomial, with respect to the temperature experienced at the temperature measurement junction. The output signal derived from the temperature measurement junction, which is typically measured in millivolts, is the temperature related input signal supplied by the thermocouple. Two additional electrical junctions occur where the other ends of the two metallically dissimilar wires are connected to the circuit conductors, typically copper wires, of the instrument. These two additional electrical junctions known as cold junctions also are thermocouple junctions, and each cold junction generates a voltage which varies with the temperature of the cold junction. In order to obtain an accurate indication of the actual temperature at the hot junction, the temperature of the cold junctions must also be determined. The cold junction temperature signal is used to compensate the overall signal from the thermocouple in order to obtain a true hot junction measurement signal, as is known.

Thermistors, resistance bulbs and thermocouples each possess features which make specific ones of these transducers best suited for particular uses. For example, resistance bulbs and thermocouples exhibit a relatively high range over which temperatures can be measured. Thermistors and thermocouples are of relatively low cost. Thermistors and resistance bulbs exhibit good interchangeability, meaning that one specific thermistor or resistance bulb can generally be interchanged for another in the instrument without undue loss of accuracy due to the relatively minor differences in inherent characteristics. It is desireable to provide an electronic thermometer which is capable of accepting thermistors, resistance bulbs and thermocouples as input transducers, and which obtains highly accurate temperature measurements from all of the transducers, and which is particularly convenient for use with a thermocouple transducer.

Humidity and pressure transducers are other types of transducers in which the output signal may be nonlinearly or polynomially related to the input variables sensed, humidity or pressure respectively. Since input transducers are selected in accordance with the variables to be measured, the device of the present invention may be advantageously used in applications where the ultimate measurement determination depends on multiple input variables which are related in a nonlinear or polynomial sense. Dew point determinations, superheat determinations and density altitude determinations are examples of such applications in which a high degree of accuracy is desirable.

INVENTION SUMMARY

One significant objective of the present invention is to provide a measurement device capable of calculating and supplying accurate determinations based on a nonlinear or polynomial relationship of two measured input variables. In accordance with this aspect of the present invention, measurement transducers operatively measure each of the input variables. The signal typically supplied by the transducers is typically nonlinearly or polynomially related to the input variable sensed. A microcomputer included within the measurement device performs calculations, based on the transducer signals and on the type of transducer employed and on information contained in memory of the microcomputer relating to the nonlinear or polynomial relationship of the input variable and the transducer signal, and creates a linearized input signal for each variable sensed. Depending on the selected type of output determination, the computer thereafter performs calculations in accordance with the multiple linearized input signals. The ultimate calculations may be based on a variety of different mathematical relationships as is known in accordance with the type of output determination desired. For polynomial equation relationships, values of constants in the equation are stored in memory for sequential predetermined segments of the curve of the polynomial equation. Different constant values are selected according to the segment of the curve in which the input signals fall before proceeding with the calculation. In this manner, the final calculation is of increased accuracy, and the relationship of the calculated output signal to the actual characteristic being determined is substantially increased. A display is included within the device and is operatively controlled by the microcomputer to indicate the output determination.

It is another objective of the present invention to provide an electronic thermometer using a thermocouple as an input transducer and which provides a relatively high degree of accuracy and convenience in temperature measurement. In accordance with this aspect of the present invention, a temperature measurement device or probe is provided in which the two dissimilar wires of the thermocouple are connected at the temperature measurement or hot junction. The other ends of the two metallically dissimilar wires are connected to circuit conductors of the thermometer at the cold compensation junction in the probe. A thermistor is connected in a thermal sensing relationship with the two cold junctions, and the thermistor is also electrically connected to the thermometer. The thermocouple signal is converted into a linearized input signal by the microcomputer. The thermistor signal at the cold junction is also converted into a linearized input signal by the microcomputer. The microcomputer thereafter accurately calculates the temperature measured at the hot junction by adding the cold junction compensation linearized signal to the linearized thermocouple signal to obtain the hot junction linearized signal corresponding to the hot junction temperature. Use of the thermistor to obtain cold junction compensation information and linearizing the signals from both the thermistor and the thermocouple secures highly reliable, accurate, inexpensive, convenient and portable advantages in employing a thermocouple as a temperature transducer in an electronic thermometer.

Another objective of the present invention is to provide a new and improved measurement device which will function as a thermometer using any or all of a thermistor, a resistance bulb or a thermocouple as input transducers and still maintain a relatively low cost and high accuracy. Another objective is to provide a new and improved measurement device which will measure dew point based on temperature and humidity input variables, and which will measure superheat temperature based on temperature and pressure input variables, and which will measure density altitude based on temperature and pressure input variables.

The scope of the invention is defined by the appended claims. A more specific understanding of the features of the invention and its further objectives and advantages is apparent from the following description of the preferred embodiments taken in conjunction with the accompanying drawings.

DRAWINGS

FIG. 1 is a schematic block diagram of the measuring and determination device of the present invention illustrating three different types of transducer means which may be employed therewith.

FIG. 2 is a schematic diagram of an improved electronic thermometer utilizing thermocouple and thermistor transducer means in a probe and employing the illustrated arrangement in conjunction with other elements shown in FIG. 1.

FIG. 3 is a flow diagram of an exemplary program and method of operation of the device and its microcomputer shown in FIG. 1.

PREFERRED EMBODIMENTS

Features of the measuring and determination device, referenced 10, are introduced by reference to FIG. 1. A plurality of transducer means, e.g., 12, 14 and 16, are used in conjunction with the measuring and determination device 10. Each transducer may take a variety of different forms, including those suitable for measuring temperature, pressure, and humidity. The transducer means 12, 14 and 16 shown in FIG. 1 are all primarily of the type for measuring temperature.

The transducer means 12 includes a conventional thermocouple 18 electrically connected to an amplifier 20. As is known, a thermocouple such as that shown at 18 is formed by an electrical connection or junction 22 of two metallically dissimilar conductors 25 and 26. Thermal effects at the connection junction 22, known as a hot or temperature measurement junction, induces a voltage between the conductors 24 and 26. Similarly, the thermocouple effects at the connection or cold junctions of the conductors to conventional circuit conductors, if any, also induce thermocouple voltages. The voltage magnitude induced by the thermocouple effects characteristically varies in a predetermined relationship with the temperature experienced at each thermocouple junction. The thermocouple induced input voltage is applied to the input terminals of the amplifier 20. The amplifier 20 is a high gain, low noise, low drift amplifier. The amplified output signal is supplied from the amplifier 20 to one input terminal of a conventional analog to digital converter means 28.

The transducer means 14 includes a conventional resistance bulb device (RTD) 30. The RTD 30 is a well-known device which experiences a characteristic resistance in a predetermined relationship to the temperature experienced. In order to measure the resistance of the RTD as a voltage signal, a current source 32 is electrically connected to supply a constant predetermined current through the RTD 30. The resultant voltage signal developed across the RTD 30 is applied to the input terminals of an amplifier 34. The amplifier 34 is a high gain, low noise and low drift amplifier. The output signal from the amplifier 34 is applied to one input terminal of the analog to digital converter 28, as a selected alternative to the output signal available from amplifier 20.

The transducer means 16 includes a thermistor 36. The thermistor 36 is a conventional device which characteristically exhibits a characteristic resistance in a predetermined relationship to the temperature experienced. In order to measure the resistance of the thermistor 36 as a voltage signal, a constant current source 38 is electrically connected to supply a constant predetermined current through the thermistor 36. The resultant voltage signal developed across the thermistor 36 is applied to the input terminals of a conventional analog to digital converting means 40.

The thermocouple 18, the RTD 30 and the thermistor 36 each characteristically exhibit predetermined relationships between the signal supplied therefrom and the temperature experienced by such devices. These relationships are all typically nonlinear and are usually mathematically defined by a polynomial equation at least to the second order. The voltage output from the thermocouple 18 is defined by a nonlinear or polynomial relationship dependent upon the temperature experienced by each electrical junction of and to the conductors 24 and 26. Similarly, the resistance of the RTD 30 and of the thermistor 36 is defined by a nonlinear or polynomial relationship dependent upon the temperature experienced by the devices 30 and 36. Such relationships are well-known.

The measuring and determining device 10 also includes a conventional microcomputer 42 which exercises control over various elements of the device 10 and creates the operative relationship of the elements of the device 10. A conventional display 44 is electrically connected to the microcomputer. The display may be a seven segment display capable of directly accepting electrical signals from the microcomputer 42, or may be of a liquid crystal display type, in which case a conventional liquid crystal decoder is also employed for converting the signals from the microcomputer 42 into signals compatible for driving the liquid crystal displays. The display 44 may include both seven segment and liquid crystal display elements. An input data select means 46 is also electrically connected to the microcomputer. The input data select means 46 allows the user to exercise manual control over the device 10 by, for example, selecting the type of display 46 to be used (e.g., seven segment display or liquid crystal display), selecting the type of measurement units to be exhibited by the display, selecting one or more of the tranducer means to supply input signals to the device 10, and selecting the type of ultimate measurement determination or calculation to be achieved by operation of the microcomputer. Depending upon the types of transducers operatively connected to the device 10 and the internal programming capabilities of the microcomputer 42, variables such as temperature, humidity, pressure, dew point, superheat temperature and density altitude can be calculated by the microcomputer 42 and indicated at the display 44. The program of the microcomputer 42, of course, operatively effects the calculation and controls operation of the elements of device 10 to obtain the desired operation.

The aforementioned U.S. Pat. No. 4,161,880 discloses the basic concepts of microcomputer control over the analog to digital converter means 28 and 40 and the display 44, and the disclosure of this prior United States patent is incorporated herein by this reference. In general, however, the microcomputer 42 exercises control over the analog to digital converters 28 and 40 by delivering control or command signals on conductors 48 and 50. In response to the control signals on conductors 48 and 50, the analog input signals to the converters 28 and 40 are converted into digital signals and supplied to the microcomputer 42 on conductors 52 and 54, respectively. Only one selected input from one of the conductors 52 or 54 is operatively received by the microcomputer 42 at a time. Of course, only one transducer, e.g., 12, 14 or 16, is electrically connected to each analog to digital converter at a time. In this manner, each converter means 28 or 40 supplies its own different input signal to the microcomputer 42.

The present invention exhibits significant improvements in the field of measuring and determining devices. The device 10 has the capability of receiving different input signals from multiple transducers and linearizing each input signal to account for the inherent nonlinearity of the response characteristics of each typical transducer. As is described more fully in the aforementioned U.S. Pat. No. 4,161,880, linearization proceeds by storing information in a memory 56 of the microcomputer 42. The linearizing information pertains to and generally defines the inherent nonlinear or polynomial response characteristics of the transducer relative to the variables sensed. The stored linearizing information will advantageously be piecewise information defined at different break points along the characteristic response curve of the transducer, although the linearizing information may also take a variety of other different forms known in the art. In the present invention, the memory 56 is programmed to store and contain linearizing information for each different type of transducer which may be used with the device 10. The stored linearizing information also takes the form of predetermined values of constants to be used in the nonlinear or polynomial equations defining the output determination based on the relationship of the accurately measured input variables. The nonlinear or polynomial curve defined by the relationship of the accurately measured input variables is also broken up into piecewise segments at predetermined break points and a group of constants is predetermined for each segment. These constants are selected in accordance with the linearized input signals when the output determination is calculated. The memory 56 is programmed to store and contain these groups constants, which are also linearizing information, for each segment of each curve representative of each output determination and calculation possible by the device.

Once the signals from the transducers are converted into digital form and applied on conductors 52 or 54 to the microcomputer 42, the program of the microcomputer causes the input signals to be linearized into linearized input signals based on a mathematical calculation and the linearizing information stored in the memory 56 and selected by the microcomputer 42 in accordance with the type of transducer supplying the input signal. Both linearized input signals are thereafter utilized in a third mathematical calculation to determine the desired output determination. The third calculation proceeds under the control of the microcomputer, usually in accordance with a nonlinear or polynomial relationship between the two accurately measured input variables, which is the case in determining dew point, superheat temperature and density altitude. Accordingly, by first linearizing the input signals to the device, the device operates with highly accurate measurements of the variables sensed. Secondly, the device 10 utilizes stored linearizing information pertaining to predetermined constants for segments of each nonlinear or polynomial curve representative of the output quantity to be determined to more accurately calculate the output determination with mathematical precision available from the microcomputer 42. In this manner, among others, the device 10 of the present invention exhibits substantial improvements in the art. One particularly improved embodiment of the present invention pertains to measuring temperature with a thermocouple, and is primarily shown in FIG. 2. A temperature measuring probe 58 or other similar device includes both the conventional thermocouple 18 and the thermistor 36. The two metallically dissimilar conductors 24 and 26 of the thermocouple extend through the interior of a tip cover member 60. The hot junction 22 formed by the electrical connection of the dissimilar conductors 24 and 26 is located interiorly of the tip cover member 60 at its distal end and in a position to best sense the thermal environment experienced by the end of the tip cover member 60. The two metallically dissimilar conductors 24 and 26 should be as free of impurities as possible to obtain a true thermocouple effect at the hot junction 22. For this reason, among others, the two metallically dissimilar conductors 24 and 26 are generally relatively expensive. Due to the expense, it is desirable to limit the amount and hence length of the conductors 24 and 26. By the present invention, the length of the conductors 24 and 26 can be limited to a very short distance by connecting the conductors 24 and 26 at junctions 62 and 64 to conventional copper circuit conductors 66 and 68, respectively. However, the junctions 62 and 64 also create a thermocouple effect because the metallic material of the conductors 24 and 26 will typically be dissimilar from the copper circuit conductors 66 and 68. Thus, three thermocouple junctions are present at 22, 62 and 64. In order to compensate for the thermocouple effect at the junctions 62 and 64, which are the cold junctions, the thermistor 36 is operatively positioned to thermally sense the temperature of the cold junction 62 and 64. The thermistor 36 is electrically connected to circuit conductors 70 and 72, also typically copper. The conductors 66, 68, 70 and 72 are gathered into a single sheath 74 which extends from a handle 76 of the probe 58. The sheath 74 and the conductors 66, 68, 70 and 72 contained therein will typically extend a considerable distance from the probe 58 to the other electronic elements of the device 10. In a manner similar to that shown in FIG. 1, the amplifier 20 amplifies the analog voltage signal present between conductors 66 and 68 and supplies the input analog voltage signal representative of the thermocouple effects at 22, 62 and 64 to the converter 28. The analog input voltage signal, representative of the temperature of the thermistor 36 and developed as a result of the constant current from the source 38, is applied to the converter 40.

In calculating the true temperature sensed by the hot junction 22 of the thermocouple arrangement shown in FIG. 2, the input signal from the thermcouple junctions and delivered on conductor 52 is first linearized by the microcomputer and stored in memory. Thereafter, the second input signal from the thermistor 36, representive of the temperature at the cold junctions 62 and 64, and delivered on conductor 54 is next linearized by the microcomputer and stored in memory. The microcomputer retrieves both signals from memory and the linearized cold junction temperature signal is added to the linearized signal representative of the thermocouple temperatures. The result of the addition is a signal representative of the temperature experienced only by the hot junction 22 of the thermocouple. The advantages of this arrangement are numerous. As previously stated, copper circuit conductors can be used to connect the thermocouple to the electronic elements of the device 10, thereby significantly reducing the cost of the device. The cold junction temperature measurement is made by the thermistor at the location where the cold junction temperature actually occurs, resulting in higher accuracy in measuring the cold junction temperature as compared to prior art methods of estimating the cold junction temperature or attempting to maintain the cold junction temperature at a predetermined fixed temperature. Errors caused by impurities in the metallic thermocouple conductors 22 and 24 are significantly reduced due to the relative shortness of the conductors 22 and 24, and because copper circuit conductors 66 and 68 are used primarily to conduct the signal to the electronic elements of the device 10. Both the cold junction temperature and the noncompensated thermocouple temperatures at the junctions 22, 62 and 64 are calculated in accordance with specific linearizing information stored in the memory of the microcomputer 42. Accordingly, the linearized signals resulting from the linearizing calculations are highly accurate of the actual temperatures experienced. Thereafter, the linearized input signals are subjected to further accurate calculations by the microcomputer to obtain the desired output signal and determination.

Similar highly accurate measurements and determinations are possible when the device 10 is used as a device for measuring dew point, superheat temperature or density altitude. In measuring the dew point, transducers for measuring temperature and humidity are electrically connected to and used with the device 10. To measure either superheat temperature or density altitude, transducers for measuring temperature and pressure are electrically connected to and used with the device 10. A humidity transducer is functionally similar to an RTD or thermistor because a humidity transducer includes a resistive element having a resistance which characteristically varies in relation with humidity, typically in accordance with a nonlinear or polynomial relationship to at least to the second order. Similarly, pressure transducers may also contain resistive elements which provide different resistance values in a predetermined relation with temperature. More expensive pressure transducers may exhibit approximately linear response characteristics but less expensive pressure transducers may exhibit a response characteristic of a nonlinear or polynomial relationship at least to the second order. Due to the significant linearizing features available from the microcomputer, it becomes advantageous to employ the less expensive and potentially more nonlinear transducers, because no compromise in accuracy results.

To calculate dew point temperature ($T_D$), the linearized signals representative of measured temperature (T) and measured humidity (U) are subjected to a calculation by the computer 42 which follows the following equation number 1:

$$T_D = \left[\frac{AU + B}{20}\right][T - 80] + [CU + DU^n + E]$$

In the above equation, the terms A, B, C, D and E represent constants which have been predetermined for each segment of the dew point temperature curve. Each segment is defined between breakpoints, and over a different set or group of the five constants A, B, C, D and E are established for each segment. In order to determine the actual values of the constants established for each curve segment, one of the known mathematical analysis techniques is employed to minimize the differences between the actual dew point temperature curve and the curve defined by equation number 1. The values of the constants are adjusted until equation number 1 best accomodates the actual curve over a given segment, and this set or group of values of constants is then recorded in a look-up table of the memory 56 of the computer 42 for that curve segment. By similar techniques, other sets or groups of constants are established for every other segment of the curve defined by equation number 1 and these other groups of constants are also stored in look-up tables of the computer memory 56. Before the dew point temperature is actually calculated by mathematically executing equation number 1, one group of constants is selected from the look-up table in accordance with the relationship of the linearized input signals to the breakpoints of the curve segments. Once the appropriate values of constants have been determined, the calculation of dew point temperature ($T_D$) proceeds utilizing the linearized input signals representative of temperature (T) and humidity (U).

To calculate superheat temperature ($T_{SH}$), the linearized signals representative of measured temperature (T) and measured pressure (P) are subjected to a calculation by the computer 42 which follows the following equation number 2:

$$T_{SH} = T - [AP + BP^n + C]$$

In the above equation, the terms A, B and C represent constants which have been predetermined in accordance with the medium for which superheat temperature is being calculated. Different examples of such mediums include R12, R22 and R502 refrigerants, as well as air. Groups of constants are determined for each curve segment, stored in a look-up table of the memory 56 of the computer 42, and are utilized in the calculation of superheat temperature, in the same manner previously described with respect to dew point temperature.

To calculate density altitude (DA), the linearized signals representative of the measured temperature (T) and measured pressure (P) are subjected to a calculation by the computer 42 which follows the following equation number 3:

$$DA = A + B\left(\frac{P}{C+T}\right)^n$$

In the above equation, A, B and C represent constants whose values have been predetermined for each curve segment. Groups of the constants are stored in a look-up table of the memory 56 of the computer 42, and are utilized in the calculation of density altitude, in the same manner previously described with respect to dew point temperature.

An operating program of the device 10 is shown in FIG. 3. Prior to initiation of operation of the device 10, one or more selected transducers is electrically connected to the device 10 in accordance with the type of output determination desired to be calculated. Upon initiation of operation, referenced at 80, the random access portion of the memory 56 of the computer 42 (FIG. 1) is cleared and the program the computer begins execution. The ultimate output determination to be obtained as a result of operation of the device 10 is selected at 82, and is manually accomplished by manipulation of the input data select device 46 (FIG. 1). One of the six output determinations shown in FIG. 3 is selected, although many others could be included in accordance with the concepts of the present invention. One of the output determinations available is a temperature measurement by the thermistor, represented at 84. In accordance with the description herein and in the aforementioned U.S. Pat. 4,161,880, the signal from the thermistor is measured and linearized at 86 and is displayed, as shown at 88. Another function available from the device 10 is temperature measurement from the RTD, as represented at 90. The signal from the RTD is measured and linearized, as shown at 92, and is displayed, as shown at 94. This function, again, proceeds in accordance with the description herein and that in U.S. Pat. No. 4,161,880. To measure thermocouple temperature, referenced at 86, the temperature from all three thermocouple junctions is measured and linearized and stored in the computer memory, as represented at 98. Similarly, the temperature at the cold junctions 62 and 64 (FIG. 2) is measured and linearized and stored in the computer memory, as referenced at 100. The true thermocouple hot junction temperature is obtained by adding the stored linearized temperatures obtained at steps 98 and 100, and the true thermocouple hot junction temperature is displayed, as shown at 102. To obtain an indication of dew point temperature, represented at 104, the humidity is measured and the signal from the humidity transducer is linearized and stored, as is represented at 106. Similarly, the temperature of the medium is measured, linearized and stored, as shown at 108. Dew point temperature is calculated in accordance with equation 1, as described herein, and the calculated dew point temperature is displayed, as shown at 110, to obtain a determination of superheat temperature, shown at 112, the pressure of the medium whose superheat temperature is to be calculated is measured, linearized and stored, as shown at 114. The temperature of the medium whose superheat temperature is to be calculated is measured, linearized and stored, as shown at 116. The superheat temperature is calculated by calculations proceeding in accordance with equation 2 as described herein, and the calculated superheat temperature is displayed, as shown at 118. To obtain an output determination of density altitude, as shown at 120, the atmospheric pressure is measured, linearized and stored, as shown at 122. The atmospheric temperature is also measured, linearized and stored, as shown at 124. Density altitude is calculated in accordance with equation 3 as described herein and the determination of density altitude is displayed, as shown at 126.

Embodiments of the present invention and its advantages and objectives have been described with a certain degree of particularity. It should be understood, however, that the present disclosure has been made by way of example, and that the invention itself is defined by the scope of the following appended claims.

What is claimed is:

1. An electronic measuring device, comprising:
   first transducer means for supplying a first signal having a first predetermined relationship to a first input variable sensed by said first transducer means;
   second transducer means for supplying a second signal having a second predetermined relationship to a second input variable sensed by said second transducer means;
   computer means including memory means containing linearizing information stored therein related to the first and second predetermined relationships;
   means for selectively conducting the first and second signals from said first and second transducer means, respectively, to said computer means; and
   said computer means operatively (a) calculating a first linearized signal utilizing the first signal and the stored linearizing information relating to the first predetermined relationship, and (b) calculating a second linearized signal utilizing the second signal and the stored linearizing information relating to the second predetermined relationship, and (c) calculating an output signal following a predetermined mathematical relationship of both the first and second linearized signals.

2. An electronic measuring device as recited in claim 1 wherein the first and second predetermined relationships and the linearizing information relating thereto are substantially different from one another.

3. An electronic measuring device as recited in claim 2 wherein at least one of the first and second predetermined relationships is nonlinear.

4. An electronic measuring device as recited in claim 3 wherein the first and second predetermined relationships are both nonlinear.

5. An electronic measuring device as recited in claims 1 or 4 wherein said computer means operatively calculates the output signal based upon a predetermined nonlinear mathematical relationship of the first and second linearized signals.

6. An electronic apparatus as recited in claim 5 wherein the memory means of said computer means further includes linearizing information stored therein related to the nonlinear relationship of the first and second input variables, and said computer means operatively calculates the output signal utilizing the stored linearizing information in the memory means relating to the predetermined relationship of the first and second variables.

7. An electronic measuring device as recited in claim 6 wherein:
said computer means calculates the output signal following a polynomial equation defining the relationship of the first and second input variables sensed to the output signal, the polynomial equation including at least one constant; and
the stored linearizing information relating to the nonlinear relationship of the first and second input variables comprises the value of the constant.

8. An electronic measuring device as recited in claim 7 wherein the stored linearizing information relating to the nonlinear relationship of the first and second input variables comprises a plurality of different values of the constant, and each different value is applicable only with respect to a segment of a curve defined by the polynomial equation.

9. An electronic measuring device as recited in claim 8 wherein:
the polynomial equation includes a set of constants, each set of constants including a plurality of constants; and
the stored linearizing information relating to the nonlinear relationship of the first and second variables comprises a plurality of different sets of constants, each set of constants applicable only with respect to a segment of a curve defined by the polynomial equation, at least one of the values of one constant of one set being different than the value of a corresponding constant of another set.

10. An electronic measuring device as recited in claim 9 further comprising:
display means for displaying a visual indication of an output determination, said output determination exhibits a predetermined relationship to the output signal; and wherein:
said computer means operatively controls said display means in accordance with the output signal.

11. An electronic measuring device as recited in claim 10 wherein:
the first and second signals supplied by said first and second transducer means are each analog signals having a predetermined nonlinear relationship to the first and second input variables sensed by said first and second transducer means, respectively; and
said means operatively conducting said first and second signals to said computer means further comprises:
(a) first converter means operatively connected for receiving the first analog signal from said first transducer means and for supplying a first digital signal corresponding to the first analog signal;
(b) second converter means operatively connected for receiving the second analog signal from said second transducer means and for supplying a second digital signal corresponding to the second analog signal;
each of said first and second converter means being operative to supply the first and second digital signals to said computer means upon command from said computer means; and
said computer means is operatively connected to control said converter means by supplying command signals to said converter means.

12. An electronic measuring device as recited in claim 11 wherein the first input variable to be sensed is one of a group consisting of temperature, pressure and humidity, and the second input variable to be sensed is a different one of said group.

13. An electronic measuring device as recited in claims 1 or 4 used as an electronic thermometer, wherein:
said first transducer means includes a thermocouple electrically connected at a cold junction to circuit conductors of said measuring device; and
said second transducer means includes a thermistor operatively positioned for sensing the temperature at the cold junction.

14. An electronic measuring device as recited in claim 13 further comprising probe means electrically connected by circuit conductors to said measuring device, said probe means including the thermocouple thermally attached thereto for sensing temperatures to be measured, said probe means further including the thermistor thermally attached thereto for sensing the temperature at the cold junction.

15. An electronic measuring device as recited in claims 1 or 4 wherein the first input variable to be sensed is one of a group consisting of temperature, pressure and humidity, and the second input variable to be sensed is a different one of said group.

16. An electronic thermometer, comprising:
temperature measuring means comprising a thermocouple, circuit conductors electrically connecting said thermocouple to elements of said thermometer, said thermocouple being electrically connected at a cold junction to the circuit conductors, and a temperature-variable resistive device operatively positioned for sensing the temperature at the cold junction, said temperature-variable resistive device being electrically connected to circuit conductors other than the circuit conductors to which the thermocouple is electrically connected;
means electrically connected to said thermocouple for deriving a first analog electrical signal therefrom;
means electrically connected to said temperature-variable resistive device for deriving a second analog electrical signal therefrom;

said thermocouple creating a first predetermined nonlinear relationship between the first electrical signal and the temperature experienced by said thermocouple;

said temperature-variable resistive device creating a second predetermined nonlinear relationship between the second electrical signal and the temperature experienced by said temperature-variable resistive device;

first analog to digital convertor means electrically connected to receive the first electrical signal, said first analog to digital converter means being operative in response to command signals to convert the first electrical signal into a corresponding first digital signal;

second analog to digital converter means electrically connected to receive the second electrical signal, said second analog to digital converter means being operative in response to command signals to convert the second electrical signal into a corresponding second digital signal;

computer means electrically connected to supply command signals to said analog to digital converter means and to receive the first and second digital signals form said converter means, said computer means including memory means containing linearizing information stored therein relating to the first and second predetermined relationships, said computer means operatively (a) calculating a first linearized signal utilizing the stored linearizing information relating to the first predetermined relationship and the first digital signal, and (b) calculating a second linearized signal utilizing the stored linearizing information relating to the second predetermined relationship and the second digital signal, and (c) calculating an output signal by adding the first linearized signal and the second linearized signal; and display means for displaying a visual indication corresponding to the output signal, said display means being electrically connected to receive the output signal from said computer means.

17. An electronic thermometer as recited in claim 16 wherein said temperature-variable resistive element is a thermistor.

18. An electronic thermometer as recited in claims 16 or 17 wherein said temperature measuring means further comprises a probe having a handle and a tip cover member extending therefrom, said thermocouple including a pair of metallically dissimilar conductors electrically connected at a hot junction, the hot junction being positioned within the tip cover member, the metallically dissimilar conductors of the thermocouple being electrically connected to the circuit conductors at cold junctions in the handle, and the temperature-variable resistive element being positioned in the handle in a thermal relationship for sensing the temperature of the cold junctions.

19. Apparatus for determining density altitude, comprising:

first temperature transducer means for supplying a first signal having a first predetermined nonlinear relationship to temperature sensed by said temperature transducer means;

pressure transducer means for supplying a second signal having a second predetermined relationship to the pressure sesnsed by said pressure transducer means;

first converter means operatively connected for receiving the first signal from said temperature transducing means and for supplying a first digital signal corresponding to the first signal;

second converter means operatively connected for receiving the second signal from said pressure transducer means and for supplying a second digital signal corresponding to the second analog signal;

computer means operatively connected for receiving the first and second corresponding digital signals from said converter means, said computer means including memory means containing linearizing information stored therein relating to the first predetermined relationship, said memory means also containing linearizing information stored therein relating to at least one value of a constant of a polynomial equation defining density altitude based on a predetermined relationship between temperature and pressure, said computer means operatively (a) calculating a first linearized signal utilizing the first digital signal and the stored linearizing information relating to the first predetermined relationship, and (b) calculating an output signal in accordance with the polynomial equation representative of density altitude utilizing the stored information relating to the value of the constant in the polynomial equation and the first linearized signal and a signal related to the second digital signal; and display means electrically connected to receive the output signal from said computer means and to visually display an indication of the output signal.

20. Apparatus as recited in claim 19 wherein:

said second predetermined relationship is nonlinear;

said memory means further contains linearizing information stored therein relating to the second predetermined relationship; and said computer means additionally operatively (c) calculating a second linearized signal utilizing the second digital signal and the stored linearizing information relating to the second predetermined relationship, and (d) calculating the output signal utilizing the first and second linearized signals and the stored linearizing information relating to the value of the constant in the polynomial equation.

21. Apparatus as recited in claims 19 or 20 wherein:

the polynomial equation includes a set of constants, each set of constants including a plurality of constants;

the stored linearizing information relates to a value for each constant in the set, and the stored information comprises a plurality of different sets of constants, each set of constants being applicable only with respect to a segment of a curve defined by the polynomial equation, at least one constant of one set being different than the value of a corresponding constant of another set; and wherein said computer selects one set of constants for use in the calculation according to the polynomial equation in accordance with a relationship of the signals indicative of the pressure and temperature sensed to the segments of the curve defined by the polynomial relationship.

* * * * *